(12) United States Patent
Amin et al.

(10) Patent No.: US 10,317,339 B2
(45) Date of Patent: Jun. 11, 2019

(54) DYNAMIC LIGHT SCATTERING BASED MICRORHEOLOGY OF COMPLEX FLUIDS WITH IMPROVED SINGLE-SCATTERING MODE DETECTION

(71) Applicants: Samiul Amin, Bromborough (GB); Carlos Alberto Rega, Worcestershire (GB)

(72) Inventors: Samiul Amin, Bromborough (GB); Carlos Alberto Rega, Worcestershire (GB)

(73) Assignee: Malvern Panalytical Limited, Malvern, Worcestershire (GB)

( * ) Notice: Subject to any disclaimer, the term of this patent is extended or adjusted under 35 U.S.C. 154(b) by 0 days.

(21) Appl. No.: 15/013,084

(22) Filed: Feb. 2, 2016

(65) Prior Publication Data

US 2017/0003220 A1 Jan. 5, 2017

Related U.S. Application Data

(63) Continuation of application No. 13/390,915, filed as application No. PCT/GB2010/051354 on Aug. 17, 2010, now Pat. No. 9,279,765.

(Continued)

(51) Int. Cl.
*G01N 21/51* (2006.01)
*G01N 11/00* (2006.01)
(Continued)

(52) U.S. Cl.
CPC ............ *G01N 21/51* (2013.01); *G01N 11/00* (2013.01); *G01N 15/1436* (2013.01);
(Continued)

(58) Field of Classification Search
CPC .......... G01N 2035/00326; G01N 2035/00495; G01N 35/10; G01N 35/026;
(Continued)

(56) References Cited

U.S. PATENT DOCUMENTS 6,016,195 A 1/2000 Peters
6,519,032 B1 2/2003 Kuebler
(Continued)

FOREIGN PATENT DOCUMENTS

CN 1821727 1/2006
CN 101460827 6/2009
(Continued)

OTHER PUBLICATIONS

Chinese Office Action dated Feb. 7, 2014. Cites Foreign Patent Document 2 and Non-Patent Literature Document 1.
(Continued)

*Primary Examiner* — Michael P Stafira
(74) *Attorney, Agent, or Firm* — Kristofer E. Elbing

(57) ABSTRACT

A fluid characterization measuring instrument is disclosed that comprises a sample vessel for a bulk complex sample fluid having a capacity that is substantially larger than a domain size of the complex sample fluid and that is sufficiently large to cause bulk scattering effects to substantially exceed surface effects for the complex fluid sample, a coherent light source positioned to illuminate the bulk complex sample fluid in the sample vessel and a first fibre having a first end positioned to receive backscattered light from the sample after it has interacted with the sample. The first fibre can also be positioned close enough to an optical axis of the coherent light source and to the sample vessel to substantially decrease a contribution of multiply scattered light in the backscattered light. The instrument can further comprise a first photon-counting detector positioned to (Continued)

receive the backscattered light from a second end of the fibre, correlation logic responsive to the first photon-counting detector and single-scattering fluid property analysis logic responsive to the correlation logic and operative to derive at least one fluid property for the sample fluid.

15 Claims, 2 Drawing Sheets

Related U.S. Application Data

(60) Provisional application No. 61/274,480, filed on Aug. 17, 2009.

(51) Int. Cl.
  G01N 15/14 (2006.01)
  G01N 21/03 (2006.01)
  G01N 21/47 (2006.01)

(52) U.S. Cl.
  CPC ....... *G01N 21/03* (2013.01); *G01N 2011/008* (2013.01); *G01N 2021/0346* (2013.01); *G01N 2021/4707* (2013.01); *G01N 2021/4709* (2013.01); *G01N 2021/513* (2013.01); *G01N 2201/08* (2013.01)

(58) Field of Classification Search
  CPC ......... G01N 35/00871; G01N 35/1065; G01N 21/25; G01N 33/54366; G01N 35/00029; G01N 15/1475; G01N 2015/008; G01N 2015/1486; G01N 2035/0013
  See application file for complete search history.

(56) References Cited

U.S. PATENT DOCUMENTS

| | | | |
|---|---|---|---|
| 6,707,556 B2 | 3/2004 | Turner et al. | |
| 6,958,816 B1* | 10/2005 | Dogariu | G01N 11/02 356/479 |
| 7,318,336 B2 | 1/2008 | Roth | |
| 2003/0124592 A1* | 7/2003 | Puskas | C12Q 1/6827 435/6.11 |
| 2005/0164205 A1* | 7/2005 | Puskas | C12P 19/34 435/6.1 |
| 2007/0281322 A1* | 12/2007 | Jaffe | G01J 3/10 435/7.1 |
| 2008/0221812 A1* | 9/2008 | Pittaro | G01N 15/14 702/66 |
| 2009/0251696 A1* | 10/2009 | McNeil-Watson | G01N 15/1427 356/336 |

FOREIGN PATENT DOCUMENTS

| | | |
|---|---|---|
| JP | 2002501622 | 1/2002 |
| JP | 2003065930 | 3/2003 |
| JP | 2008175723 | 7/2008 |
| WO | 9951980 | 10/1999 |
| WO | 2009059008 | 5/2009 |
| WO | 2009090562 | 7/2009 |

OTHER PUBLICATIONS

Chinese Office Action dated Sep. 17, 2004. Cites Chinese equivalent of US Patent Document 1, Foreign Patent Document 1, and Non-Patent Literature Document 2.
Liu et al., "Design of Optical Fiber Probe to Measure the Parameters of Hemorheology", China Medical Equipment 2008, vol. 23, issue 2, p. 8. Machine translation.
Li Xiao-na et, "Research Progress in Experimental Techniques and Its Relevant Theories of Cell Mechanics on Cytokinesis", Space Medicine and Medical Engineering 22(2):148. Machine translation.
Gardel ML, Valentine MT, and Weitz DA. Microrheology. Department of Physics and Division of Engineering and Applied Sciences, Harvard University. pp. 1-53. 2005.
Ansari et al. Dynamic Light Scattering Particle Size Measurements in Turbid Media. Prodeeding of the International Society for Optical Engineering (SPIE). pp. 146-156, vol. 3251, Jan. 27, 1998.
Rheolaser Lab, Micro-rheology for soft materials, brochure, Aug. 13.
Japanese (JP2012525210) Written Amendment, dated Jul. 23, 2013.
Japanese (JP2012525210) Search Report by Registered Searching Organization, dated Jan. 30, 2014.
Japanese (JP2012525210) Notification of Reasons for Refusal, dated Feb. 12, 2014.
Japanese (JP2012525210) Written Argument, dated Jun. 11, 2014.
Japanese (JP2012525210) Decision to Grant, dated Nov. 18, 2014.
Chinese (CN201080036806) Office Action, dated Feb. 7, 2014.
Chinese (CN201080036806) Office Action, dated Sep. 17, 2014.
Chinese (CN201080036806) Argument, dated Jun. 18, 2014.
Chinese (CN201080036806) Supplementary Search, dated Sep. 4, 2014.
Chinese (CN201080036806) Nth Office Action, dated May 5, 2015.
Chinese (CN201080036806) Argument, dated Jul. 2, 2015.
Chinese (CN201080036806) Supplementary Search, dated Sep. 17, 2015.
Chinese (CN201080036806) Nth Office Action, dated Sep. 28, 2015.
Chinese (CN201080036806) Argument, dated Oct. 19, 2015.
Chinese (CN201080036806) Notification to Grant Patent Right for Invention, dated Nov. 5, 2015.
International Search Report, dated Jan. 12, 2010.
International Preliminary Report on Patentability, dated Feb. 21, 2012.

* cited by examiner

DYNAMIC LIGHT SCATTERING BASED MICRORHEOLOGY OF COMPLEX FLUIDS WITH IMPROVED SINGLE-SCATTERING MODE DETECTION

This application is a continuation of application Ser. No. 13/390,915, filed Sep. 13, 2012, which is a US National Phase counterpart of international application number PCT/GB2010/51354, filed Aug. 17, 2010, which claims priority to U.S. provisional application No. 61/274,480, filed Aug. 17, 2009, which are all herein incorporated by reference.

FIELD OF THE INVENTION

This invention relates to methods and apparatus for obtaining the viscoelastic parameters of complex fluids, such as colloidal and biological complex fluids.

BACKGROUND OF THE INVENTION

Viscoelasticity means the simultaneous existence of viscous and elastic properties in a material. Many complex and structured fluids exhibit viscoelastic characteristics, i.e., they have the ability to both store energy like an elastic solid as well as dissipate energy such as a viscous liquid. When a stress is applied to such a viscoelastic fluid it stores some of the energy input, instead of dissipating all of it as heat and it may recover part of its deformation when the stress is removed.

The elastic modulus or G' represents storage of elastic energy, while the loss modulus G" represents the viscous dissipation of that energy. The magnitude of G' and G" for most complex fluids depends upon the time scales or frequency at which the property is probed. Depending upon the stress relaxation mechanisms present in the complex fluids, they may exhibit different behaviour (either G'>G" or G">G' or G'=G") at different frequencies. Having the ability to probe the viscoelastic response over a wide frequency range therefore provides insights into the stress-relaxation mechanisms in complex fluids, and since this is connected to the underlying structure of the complex fluid, insights into the underlying structure can be obtained.

Currently, high end rotational rheometers are used to measure these viscoelastic properties, but the measurement time can be quite long depending upon the frequency being probed. Also, a considerable amount of time can be spent in cleaning the rheometer's stage and preparing the test before the next sample can be loaded, making high-throughput measurements quite challenging. Other disadvantages of rotational rheometers include that they provide access to a very limited frequency range, and they require large sample volumes, typically greater than 1 ml.

Optical-based Microrheological techniques have also been used to measure viscoelastic properties of complex fluids. These involve embedding probe particles into a viscoelastic fluid of interest (polymer solution, surfactant solution etc.) and following the thermal motion of the probe particles. The thermally driven random motion of colloidal spheres suspended in a complex fluid is very different than the diffusive Brownian motion of similar spheres suspended in a purely viscous fluid (e.g simple Newtonian fluid). When suspended in complex fluids, which exhibit elasticity, the probe particles exhibit sub diffusive motion or if the elasticity becomes very significant the probe particles may become locally bound. As the microstructure slowly relaxes, it allows the particles to escape this elastic 'cage.' This motion of probe particles as a function of time can be obtained from mean squared displacement $<\Delta r^2(t)>$ of probe particles which can be obtained from the electric field autocorrelation function obtained from a Dynamic Light Scattering (DLS) experiment:

$$g^{(1)}(\tau)=\exp(-\tfrac{1}{6}q^2\Delta r^2(\tau))$$

Once the mean squared displacement, $<\Delta r^2(t)>$ is obtained, it can be related through to the complex viscoelastic modulus G* and through to the elastic G' and viscous modulus G" through:

$$G'(\omega)=|G^*(\omega)|\cos(\pi\alpha(\omega)/2),$$

$$G''(\omega)=|G^*(\omega)|\cos(\pi\alpha(\omega)/2),$$

where $$|G^*(\omega)| \approx \frac{k_B T}{\pi a(\Delta r^2(1/\omega))\Gamma[1+\alpha(\omega)]}.$$

This analysis is based on two key assumptions:
The system exhibits single scattering. As the system becomes multiply scattering the analysis no longer remains valid.
The scattering is dominated by the embedded probe particles, as the whole principle is based on following the motion of the embedded probe particles.

Many complex fluids at even moderate concentrations start to contribute quite significantly to the scattered light signal. In order to ensure the domination of the scattering by probe particles, they need to be added in moderately high concentrations (but still much less than 0.5 vol %). Adding probe particles in these moderately concentrated regimes makes the system quite turbid and multiple scattering tends to become very significant.

In these types of systems, the concentration of probe particles can be raised even further to enter into the strongly multiply scattering regime, while changing the analysis from that described above to theories developed for using the multiply scattered light in the microrheological analysis. This then evolves into a technique known as Diffusing Wave Spectroscopy (DWS). An important concern for this technique is that the analysis is inherently complicated and makes interpretation of data highly challenging. The agreement of data obtained from DWS with mechanical data is in many cases quite poor and requires resealing.

SUMMARY OF THE INVENTION

Several aspects of the invention are disclosed in this application.

In one general aspect, the invention features a fluid characterization measuring instrument that includes a sample vessel for a bulk complex sample fluid having a capacity that is substantially larger than a domain size of the complex sample fluid and that is sufficiently large to cause bulk scattering effects to substantially exceed surface effects for the complex fluid sample, a coherent light source positioned to illuminate the bulk complex sample fluid in the sample vessel, a first fibre having a first end positioned to receive backscattered light from the sample after it has interacted with the sample, wherein the first fibre is positioned close enough to an optical axis of the coherent light source and to the sample vessel to substantially decrease a contribution of multiply scattered light in the backscattered light, a first photon-counting detector (e.g., 20) positioned to receive the backscattered light from a second end of the fibre, correlation logic responsive to the first photon-counting detector, and single-scattering fluid property analysis logic responsive to the correlation logic and operative to derive at least one fluid property for the sample fluid, which can be implemented using software and a Personal Computer (PC) 24.

In preferred embodiments the instrument can be constructed and adapted to allow the photon detector to allow scattered light to be detected over a range of different angles ranging from 173° to 13.5°. The instrument can be constructed and adapted to allow the first photon-counting detector to be further responsive to forward scattered light. The center of the scattering volume can be selectively positioned substantially at the surface of the sample fluid.

In another general aspect, the invention features a fluid characterization measuring instrument that includes a sample vessel for a sample fluid, a coherent light source positioned to illuminate the sample fluid in the sample vessel, a splitter having an input responsive to light scattered by the sample and having first and second outputs, a first photon-counting detector positioned to receive a first portion of the scattered light from a first output of the splitter, a second photon-counting detector positioned to receive a second portion of the scattered light from a second output of the splitter, cross-correlation logic responsive to the first photon-counting detector and to the second photon-counting detector, and single-scattering fluid property analysis logic responsive to the correlation logic and operative to derive at least one fluid property for the sample fluid.

In a further general aspect, the invention features a fluid characterization measuring instrument that includes a sample vessel for a bulk complex sample fluid having a capacity that is substantially larger than a domain size of the complex sample fluid and that is sufficiently large to cause bulk scattering effects to substantially exceed surface effects, and wherein the sample vessel has an optical path length of about 1.5 mm or less, a coherent light source positioned to illuminate the sample fluid in the sample vessel through the optical path length, a first photon-counting detector positioned to receive light scattered by the sample, correlation logic responsive to the first photon-counting detector, and single-scattering fluid property analysis logic responsive to the correlation logic and operative to derive at least one fluid property for the sample fluid. In preferred embodiments, the sample vessel can be a capillary tube.

In another general aspect, the invention features a microrheological measuring method that includes the steps of illuminating a sample of a complex fluid with coherent light, wherein a volume of the sample of the complex fluid is substantially larger than a domain size of the complex sample fluid and is sufficiently large to cause bulk scattering effects to substantially exceed surface effects for the complex fluid sample, detecting backscattered photons from the sample from a position that is close enough to an optical axis of the coherent light and to the sample to substantially decrease a contribution of multiply scattered light arising from scattering of light from the coherent light in the backscattered light, performing a correlation operation on a detection signal representative of the detected backscattered photons, and deriving at least one fluid property from results of the correlation operations for the sample fluid based on single-scattering analysis.

In preferred embodiments the correlation operation can be an autocorrelation operation. Scattered light can be detected over a range of different angles ranging from 173° to 13.5°, with the steps of performing a correlation operation and deriving being performed for the light detected over a range of angles. Steps of detecting can be carried out in both backscattering mode and forward transmission mode in order to obtain an extended region of frequency response. Steps of detecting can be carried out using a range of different probe sizes ranging from 30 nm to 1 um in order to extend obtained frequency and/or minimise multiple scattering by adjusting volume of required probe particles. Steps of detecting can be carried out using a range of different probe chemistries to minimise interactions with the complex fluid of interest.

In a further general aspect, the invention features a viscoelecicity measuring method, that includes the steps of illuminating a sample fluid with coherent light, splitting scattered light received from the sample into first and second portions, detecting photons from the first portion of the scattered light, detecting photons from the second portion of the scattered light, performing a cross-correlation operation between a first detection signal representative of the backscattered photons in the first portion and a second detection signal representative of the backscattered photons in the second portion, and deriving at least one fluid property from results of the correlation operation for the sample fluid based on single-scattering analysis.

In another general aspect, the invention features a viscoelecicity measuring method, that includes the steps of illuminating a sample of a complex fluid with coherent light through an optical path length of about 1.5 mm or less, wherein a volume of the sample of the complex fluid is substantially larger than a domain size of the complex sample fluid and is sufficiently large to cause bulk scattering effects to substantially exceed surface effects for the complex fluid sample, detecting photons from light scattered from the sample, performing a correlation operation on a detection signal representative of the scattered photons, and deriving at least one fluid property from results of the correlation operation for the sample fluid based on single-scattering analysis.

In a further general aspect, the invention features a fluid characterization instrument for measuring viscoelastic properties of a sample fluid that includes a capillary tube for a sample fluid, a plurality of probe particles for the sample fluid, a coherent light source positioned to illuminate the sample fluid and probe particles in the capillary tube with coherent light, a photon-counting detector that produces electronic pulses for each photon detected and is positioned to receive coherent light from the source scattered by the plurality of probe particles in the sample fluid in the capillary tube, and fluid property analysis logic responsive to the detector and operative to derive at least one viscoelastic fluid property for the sample fluid based on light scattered by the plurality of probe particles in the sample fluid in the capillary tube.

In preferred embodiments, the instrument can include an optical fiber between the capillary tube and the photon-counting detector. The optical fiber can have a first end positioned to receive backscattered light from the sample after it has interacted with the sample. The optical fiber can be positioned close enough to an optical axis of the coherent light source and to the sample vessel to substantially decrease a contribution of multiply scattered light in the backscattered light. The capillary tube and have a diameter of 1.5 mm or less. The instrument can further include correlation logic between the detector and the property analysis logic. The instrument can be constructed and adapted to allow the photon detector to allow scattered light to be detected over a range of different angles ranging from 173° to 13.5°. The instrument can be constructed and adapted to allow the photon-counting detector to be responsive to backscattered light. The instrument can be constructed and adapted to allow the photon-counting detector to be further responsive to forward scattered light. The instrument can be constructed and adapted to allow the photon-counting detector to be responsive to forward scattered light. The center of the scattering volume can be selectively positioned substantially at the surface of the sample fluid.

In another general aspect, the invention features a microrheological measuring method for measuring viscoelastic properties of a sample fluid that includes suspending probe particles in a sample in a capillary tube, illuminating the sample and probe particles in the capillary tube with coherent light, counting photons scattered by the sample and probe particles in the capillary tube, and deriving at least one viscoelastic fluid property of the sample fluid from results of the step of counting photons for the sample fluid.

In preferred embodiments the instrument can further include the step of performing a correlation operation on results of the step of detecting, with the step of deriving deriving the fluid property from results of the step of performing a correlation operation. The correlation operation can be an autocorrelation operation. Scattered light can be detected over a range of different angles ranging from 173° to 13.5° with the steps of performing a correlation operation and deriving being performed for the light detected over a range of angles. The step of detecting can be carried out in both backscattering mode and forward transmission mode in order to obtain an extended region of frequency response. The steps of detecting can be carried out using a range of different probe sizes ranging from 30 nm to 1 um in order to extend obtained frequency and/or minimise multiple scattering by adjusting volume of required probe particles. Steps of detecting can be carried out using a range of different probe chemistries to minimise interactions with the complex fluid of interest.

In a further general aspect, the invention features a fluid characterization instrument for measuring viscoelastic properties of a sample fluid that includes a capillary tube for a sample fluid, a plurality of probe particles for the sample fluid, means for coherently illuminating the sample fluid and probe particles in the capillary tube, means for counting photons from the sample and probe particles in the capillary tube, and means responsive to the means for counting photons from the sample and probe particles in the capillary tube to derive at least one viscoelastic fluid property for the sample fluid. In preferred embodiments, the coherent light can passthrough a non-invasive probe.

Instruments according to the invention can be advantageous in that they can allow for advanced rheological characterization on very small sample volumes. They can also allow access to very high-frequency (short time) dynamics.

Instruments according to the invention may allow for improvements in viscoelasticity measurements in a variety of application areas These can include high-frequency rheological characterization of complex fluids for academic research, personal care, chemicals, and foods, where instruments according to the invention can provide an alternative to piezoelectric approaches (PAV/PRV) and DWS. Instruments according to the invention can also be used in life sciences applications, such as for advanced rheological characterization of proteins and other biopolymers in solution. In the field of chemicals and specialty chemicals, instruments according to the invention may be used for advanced rheological characterization of newly synthesized polymers or other chemicals.

Instruments according to the invention may also be used in high-throughput applications in a variety of areas, such as academic and pharmaceutical research, personal care, and chemicals.

DETAILED DESCRIPTION OF AN ILLUSTRATIVE EMBODIMENT

Figure 1:
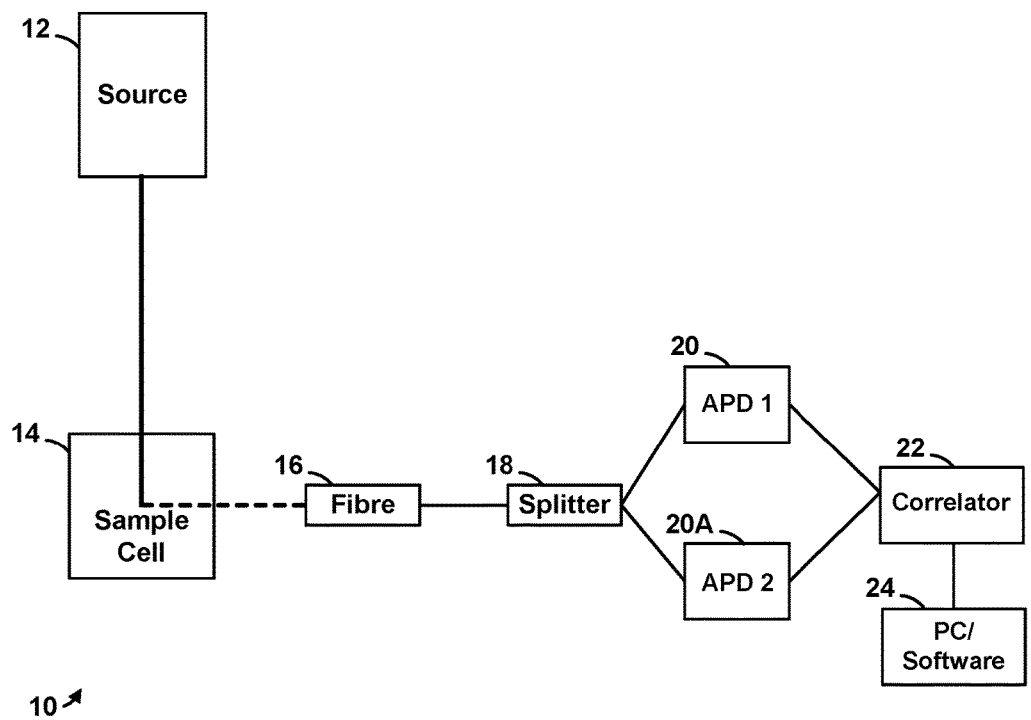
FIG. 1 is a block diagram of a microrheological fluid characteristic measurement instrument according to the invention.
Figure 2:
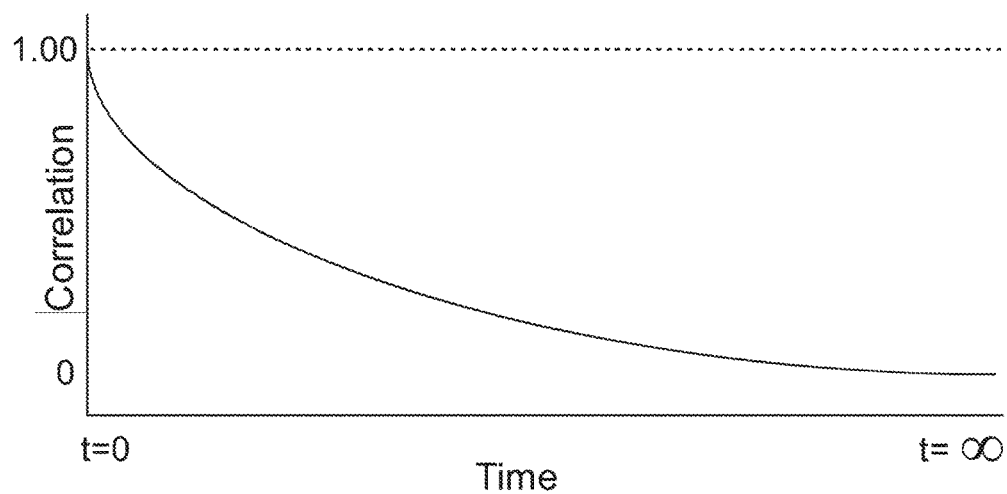
FIG. 2 is a plot of an illustrative correlation function for the instrument of FIG. 1.

Referring to FIG. 1, an illustrative embodiment of a microrheological fluid characteristic measurement instrument 10 according to the invention includes a coherent light source 12, such as a laser, a sample cell 14, at least one detector 20, and a correlator 22. The correlator can include autocorrelation logic embodied in hardware and/or software to apply an autocorrelation function to a signal from the detector. Single-scattering analysis, such as the viscoelasticity parameter derivations described above, can then be applied to results of the correlation operation to extract one or more fluid parameter characteristics for the sample. An illustrative correlation function is shown in FIG. 2.

The sample cell 14 can be a short-path-length cell, such as a capillary tube having a diameter of 1.5 mm or less. The use of such short-path-length cells allows the instrument to minimize multiple scattering contributions to the correlation function in the transmission geometry. It is also beneficial in that it allows the instrument to make measurements based on small sample amounts, which is particularly important for biomolecules, such as proteins and small-molecule drugs, for which samples can be particularly small. This can allow the instrument to be used as part of a high-throughput screening system.

The instrument can perform forward-scattering measurements, backscatter measurements, or both. The use of backscatter detection using Non-Invasive Back-Scatter (NIBS) techniques can also help to minimize effect of multiple scattering contributions to the correlation function. This technique involves performing backscattering measurements at close to 180°, (e.g., 173°), and is described in U.S. Pat. No. 6,016,195, German patent 19725211, and Japanese patent no. 2911877, which are herein incorporated by reference. The exact NIBS detector spacing and angles will depend on a variety of factors, including the nature of the sample, the material used for the sample vessel, and the desired accuracy.

The instrument 10 can also include a fibre 16, a splitter 18, such as a 50:50 splitter, and a second detector 20A. The correlator 24 can include cross-correlation logic that allows the instrument to perform a cross-correlation between the signals from the two detectors. This correlation operation allows the instrument to more accurately extract a particle size for samples which are poor scatterers and or are small (a few nm) in size because the effect of the detector dead time, which determines the shortest autocorrelation time, will be reduced. The cross-correlation operation is also beneficial because it is less sensitive to detector noise issues, such as afterpulsing, which are uncorrelated between the detectors. And it can allow the correlator to directly determine the zero time correlation (intercept) of the correlation function, improving the calculation of the high frequency G' and G".

As discussed above, instruments according to the invention can be used as part of different kinds of high-throughput screening systems. Such systems generally include large-scale sample management systems, such as ones that are based on scanning mirrors or robotic X-Y stages. The Malvern Zetasizer APS, for example, provides off-the-shelf automated measurements of samples in industry standard 96- or 384-well plates. To detect bulk properties of the fluids, the sample vessels should have a capacity that is substantially larger than a domain size of the complex sample fluid and is sufficiently large to cause bulk scattering effects to substantially exceed surface effects for the complex fluid sample. Exact sample vessel volumes depend on a variety of factors, including the nature of the sample and desired accuracy levels.

Instruments according to the invention can be configured to allow scattered light to be detected over a range of different angles, such as from 173° to 13.5°. They can also be configured to allow measurements to be carried out in both backscattering mode or transmission mode in order to obtain an extended region of frequency response. These objectives can be accomplished in different ways, such as by allowing a single detector to move or by providing more than one detector. Measurements can also be carried out using a range of different probe sizes ranging from 30 nm to 1 um in order to extend obtained frequency and/or minimise multiple scattering by adjusting a volume of required probe particles. And measurements can be carried out using a range of different probe chemistries to minimise interactions with a complex fluid of interest.

EXAMPLE 1

In order to validate the above approach, DLS-based optical microrheology was carried out on the Zetasizer Nano (Malvern Instruments Limited) without any hardware modifications. It should be noted that the Zetasizer Nano is designed to implement the NIBS based technique. The Zetasizer Nano is described, for example in U.S. provisional application No. 61/206,688, which is herein incorporated by reference.

The system investigated was a 2M molecular weight PEO (Polyethylene Oxide) formulation at a number of different concentrations. This system was already quite turbid even at low concentrations (0.5 wt %) and was contributing significantly to the scattered light signal. In order to ensure domination of the scattering by the probe particles (700 nm nominal diameter, Polystyrene particles, Duke Scientific) they were added in relatively high concentrations, which took the system into the moderately multiply scattered regime. As the samples were visibly quite turbid, measurements would likely have been very difficult to carry out for them using traditional DLS-based microrheology.

Figure 3:
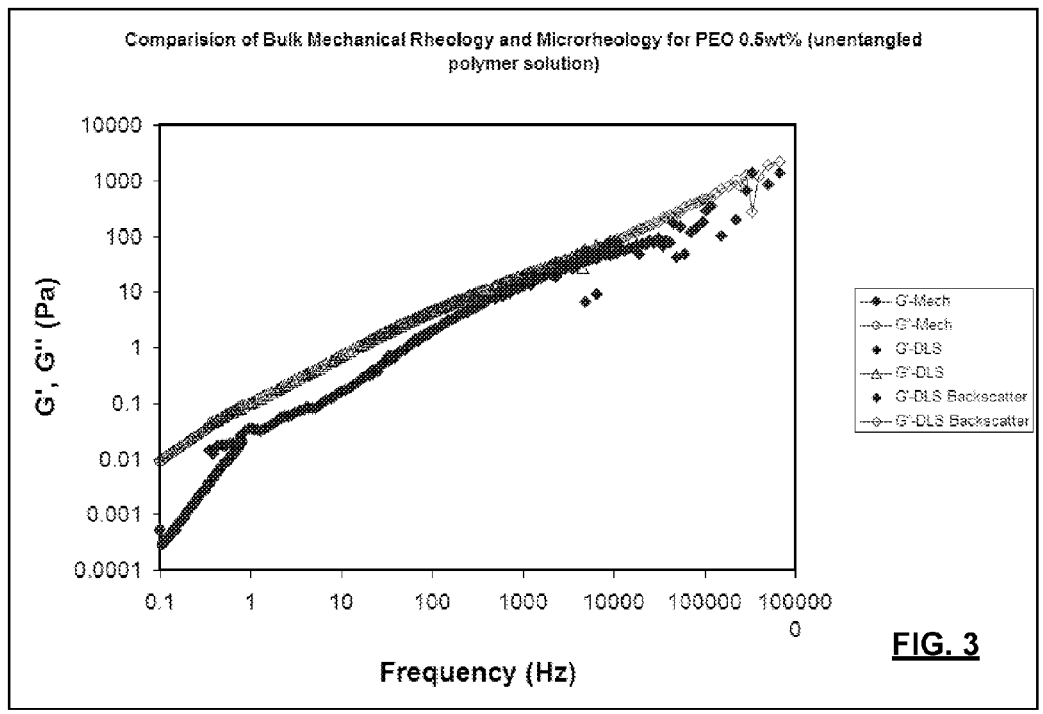
FIG. 3 is a plot of DLS-based microrheology data for a 0.5% by weight PEO solution using the instrument of FIG. 1, with mechanical rheometry results also shown for the same sample.
Figure 4:
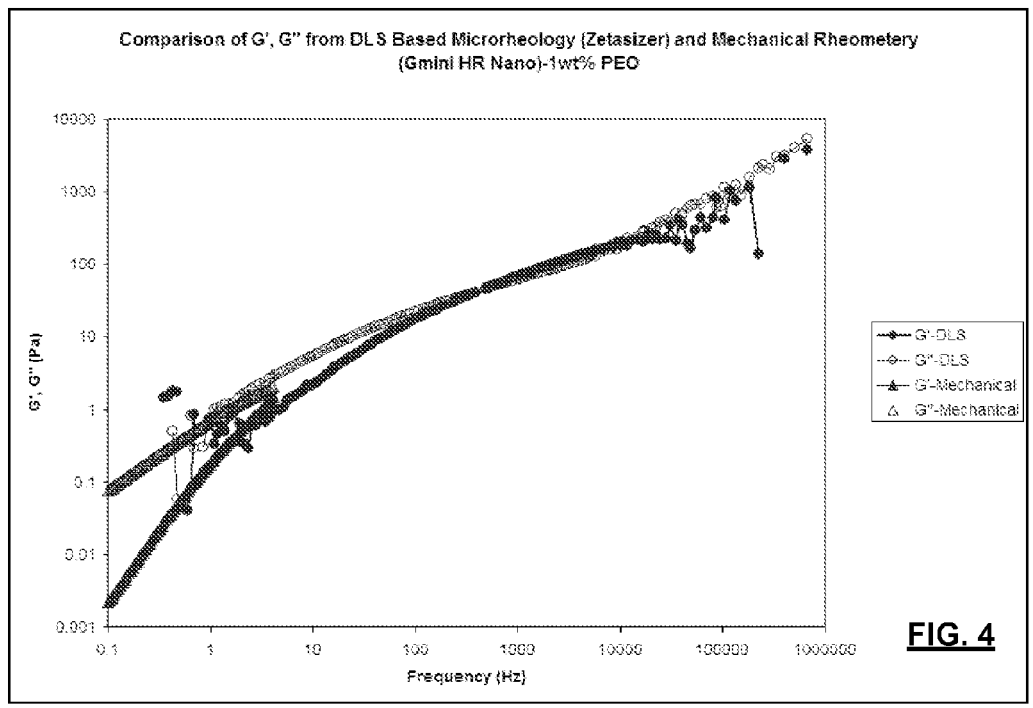
FIG. 4 is a plot of DLS-based microrheology data for a 1.0% by weight PEO solution using the instrument of FIG. 1, with mechanical rheometry results also shown for the same sample.

FIGS. 3 and 4 illustrate microrheological data obtained from the Zetasizer and comparable data for a high end rotational mechanical rheometer (Bohlin Gemini HR Nano, Malvern Instruments Limited). The data clearly illustrates very good agreement with the mechanical data at the low frequency overlap region and also illustrates the extensive frequency range over which the viscoelastic response was obtained. The DLS-based high-frequency data adequately captures the physics (Zimm and Rouse Dynamics) that is expected for this system.

In this example, the correlation operation is performed on board the instrument in a dedicated DSP board and single-scattering analyses are performed using specialized software running on a general-purpose workstation. The instrument can also use other approaches to perform these operations, such as dedicated hardware or a combination of software and dedicated hardware.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

The invention claimed is:

1. A fluid characterization instrument for measuring viscoelastic properties of a sample fluid, comprising:
   a capillary tube for a sample fluid,
   a plurality of probe particles for the sample fluid,
   a coherent light source positioned to illuminate the sample fluid and probe particles in the capillary tube with coherent light,
   a photon-counting detector that produces electronic pulses for each photon detected and is positioned to receive coherent light from the source scattered by the plurality of probe particles in the sample fluid in the capillary tube, and
   fluid property analysis software running on a processor and responsive to the pulses from the detector resulting from receiving coherent light from the source scattered by the plurality of probe particles in the sample fluid in the capillary tube and operative to derive at least one viscoelastic fluid property for the sample fluid based on the light scattered by the plurality of probe particles in the sample fluid in the capillary tube, wherein the at least one viscoelastic fluid property includes the elastic and loss modulus for the sample fluid.

2. The instrument of claim 1 further including an optical fiber between the capillary tube and the photon-counting detector.

3. The instrument of claim 2 wherein the optical fiber has a first end positioned to receive backscattered light from the sample after it has interacted with the sample.

4. The instrument of claim 3 wherein the optical fiber is positioned close enough to an optical axis of the coherent light source and to the sample vessel to substantially decrease a contribution of multiply scattered light in the backscattered light.

5. The instrument of claim 1 wherein the capillary tube has a diameter of 1.5 mm or less.

6. The instrument of claim 1 further including correlation logic between the detector and the property analysis logic.

7. The instrument of claim 1 wherein the instrument is constructed and adapted to allow the photon detector to allow scattered light to be detected over a range of different angles ranging from 173° to 13.5 °.

8. The instrument of claim 1 wherein the instrument is constructed and adapted to allow the photon-counting detector to be responsive to backscattered light.

9. The instrument of claim 8 wherein the instrument is constructed and adapted to allow the photon-counting detector to be further responsive to forward scattered light.

10. The instrument of claim 1 wherein the instrument is constructed and adapted to allow the photon-counting detector to be responsive to forward scattered light.

11. The instrument of claim 1 wherein the center of the scattering volume can be selectively positioned substantially at the surface of the sample fluid.

12. A fluid characterization instrument for measuring viscoelastic properties of a sample fluid, comprising:
a capillary tube for a sample fluid,
a plurality of probe particles for the sample fluid,
means for coherently illuminating the sample fluid and probe particles in the capillary tube,
means for counting photons from the sample and probe particles in the capillary tube, and
means responsive to the means for counting photons from the sample and probe particles in the capillary tube to derive at least one viscoelastic fluid property of the sample fluid from the photons counted in coherent light scattered by the plurality of probe particles in the sample fluid in the capillary tube, wherein the at least one viscoelastic fluid property includes the elastic and loss modulus for the sample fluid.

13. The apparatus of claim 1 wherein the coherent light passes through a non-invasive probe.

14. The apparatus of claim 1 wherein the fluid property analysis logic is operative to derive the at least one viscoelastic fluid property for the sample fluid based on analysis of thermally driven random motion of the plurality of probe particles in the sample fluid in the capillary tube.

15. The apparatus of claim 12 wherein the means to derive at least one fluid property is operative to derive the at least one viscoelastic fluid property for the sample fluid based on analysis of thermally driven random motion of the plurality of probe particles in the sample fluid in the capillary tube.

* * * * *